United States Patent

Hagemeyer et al.

[11] Patent Number: 5,902,918
[45] Date of Patent: May 11, 1999

[54] CATALYST AND CATALYTIC OXIDATIVE DEHYDROGENATION OF ALKYLAROMATICS AND PARAFFINS

[75] Inventors: Alfred Hagemeyer, Ludwigshafen; Günter Lauth, Lübeck; Thomas Lautensack, Ludwigshafen; Axel Deimling, Neustadt, all of Germany

[73] Assignee: BASF Aktiengesellschaft, Ludwigshafen, Germany

[21] Appl. No.: 08/765,746

[22] PCT Filed: Jun. 26, 1995

[86] PCT No.: PCT/EP95/02483

§ 371 Date: Mar. 13, 1997

§ 102(e) Date: Mar. 13, 1997

[87] PCT Pub. No.: WO96/01796

PCT Pub. Date: Jan. 25, 1996

[30] Foreign Application Priority Data

Jul. 7, 1994 [DE] Germany .............................. 44 23 975

[51] Int. Cl.⁶ .................................................... C07C 5/367
[52] U.S. Cl. ........................... 585/444; 585/444; 585/440
[58] Field of Search ..................................... 585/444, 440, 585/303, 340, 344, 350, 353; 502/303, 340, 344, 350, 355

[56] References Cited

U.S. PATENT DOCUMENTS

| | | | |
|---|---|---|---|
| 3,440,299 | 4/1969 | Woskow et al. | 260/680 |
| 3,567,793 | 3/1971 | Colling et al. | 260/680 |
| 3,686,347 | 8/1972 | Dean et al. | 260/680 |
| 4,396,537 | 8/1983 | Eastman | 252/437 |
| 4,568,789 | 2/1986 | Withers, Jr. | 585/654 |
| 4,769,508 | 9/1988 | Gastinger et al. | 585/500 |
| 4,795,849 | 1/1989 | Gaffney et al. | 585/500 |
| 4,912,081 | 3/1990 | Sofranko et al. | 502/207 |

FOREIGN PATENT DOCUMENTS

| | | |
|---|---|---|
| 030 837 | 6/1981 | European Pat. Off. . |
| 179 869 | 5/1986 | European Pat. Off. . |
| 254 423 | 5/1986 | European Pat. Off. . |
| 397 637 | 11/1990 | European Pat. Off. . |
| 403462 | 12/1990 | European Pat. Off. . |
| 885422 | 12/1961 | United Kingdom . |
| 999629 | 7/1965 | United Kingdom . |
| 2156842 | 10/1985 | United Kingdom . |

OTHER PUBLICATIONS

K. Aykan, J. Catal. vol. 12 (1968), pp. 281–290.

*Primary Examiner*—Glenn A. Caldarola
*Assistant Examiner*—Thuan D. Dang
*Attorney, Agent, or Firm*—Keil & Weinkauf

[57] ABSTRACT

Alkenylaromatics are produced by catalytic oxidative dehydrogenation of alkylaromatics employing a redox catalyst which is bismuth oxide, in combination with an additive compound of an alkali metal and/or an alkaline earth metal, on a titanium dioxide carrier. In a first reaction step, an alkylaromatic starting material is oxidatively dehydrogenated with the redox catalyst in the absence of molecular oxygen with attending reduction of the redox catalyst. In a second reaction step, the reduced redox catalyst is reoxidized with an oxygen-containing gas.

11 Claims, No Drawings

CATALYST AND CATALYTIC OXIDATIVE DEHYDROGENATION OF ALKYLAROMATICS AND PARAFFINS

BACKGROUND OF THE INVENTION

1. Field of the Invention

The present invention relates to a process and a catalyst for the catalytic oxidative dehydrogenation of alkylaromatics and paraffin hydrocarbons to give the corresponding alkenylaromatics and olefins, preferably of ethylbenzene to give styrene, water being formed and the dehydrogenation taking place in the absence of free oxidizing agent (ie. oxidizing agent added continuously to the stream of starting materials), such as molecular oxygen or oxygen-containing gases and the redox catalyst consisting of at least one reducible metal oxide being the sole oxygen source and performing the function of an oxygen store or oxygen carrier.

Olefins and alkenylbenzenes, in particular styrene and divinylbenzene, are important monomers for engineering plastics and are produced in large amounts. Styrene is prepared predominantly by nonoxidative dehydrogenation of ethylbenzene over a modified iron oxide catalyst, one mole of hydrogen being formed per mole of styrene. Unfortunately, this is an equilibrium reaction which is carried out at high temperatures of, typically, from 600 to 700° C. and takes place with the conversion of about 60% at a styrene selectivity of about 90%.

The equilibrium can be overcome and a virtually quantitative conversion achieved by oxidative dehydrogenation in which an oxidizing agent, such as molecular oxygen or an oxygen-containing as, is introduced into the stream of starting materials, since water is now formed as an accompanying product. Furthermore, lower reaction temperatures are required for this reaction. However, the disadvantage of this process is the loss of selectivity with respect to the desired product owing to the presence of oxygen, since the high oxygen concentration in the reaction zone promotes total oxidation as a secondary reaction.

It is therefore being proposed to use, as the oxygen carrier, a catalyst consisting of a reducible metal oxide instead of free oxidizing agent (oxygen). The catalyst (simultaneously an oxygen carrier) is gradually consumed and must be regenerated in a second step, restoring the initial activity. In the regeneration phase, for example, coke deposits can also be burnt off. The regeneration is highly exothermic so that the waste heat liberated can be used, for example, for generating steam.

By decoupling the reduction step and oxidation step, the selectivity can be substantially increased.

Two variants are available for the technical realization of this proposal, ie. the separation of the two steps in terms of space and in terms of time.

In the former, a moving bed or a circulating fluidized bed is used so that, after the resulting reaction products have been separated off, the catalyst particles are transported from the dehydrogenation zone to a separate regeneration reactor, in which the reoxidation is carried out. The regenerated catalyst is recycled to the dehydrogenation zone. The catalyst is exposed to high mechanical stresses and must therefore have sufficient hardness.

2. Description of the Related Art

The embodiment using a fixed bed involves periodic switching between the starting material feed and, if necessary after a flushing phase, the regeneration gas.

This principle of separation of the two steps of the redox reaction using a reducible and regeneratable catalyst was first described for the oxidation or ammoxidation of propene to acrolein and acrylic acid or acrylonitrile, respectively (GB 885422; GB 999629; K. Aykan, J. Catal. 12 (1968), 281–190), arsenate and molybdate catalysts being used. The use of the process in the oxidative dehydrogenation of aliphatic alkanes to mono- and diolefins using ferrite catalysts (e.g. U.S. Pat. No. 3,440,299, DE 21 18 344, DE 17 93 499) is likewise known, as is the use for the oxidative coupling of methane to give higher hydrocarbons, different catalyst classes being used (eg. U.S. Pat. No. 4,795,849, DE 3 586 769 with Mn/Mg/Si oxides; U.S. Pat. No. 4,568,789 with Ru oxide; EP 254 423 with Mn/B oxides on MgO; GB 2 156 842 with $Mn_3O_4$ spinels). The dehydrodimerization of toluene to stilbene in the absence of free oxygen by means of reducible catalysts, such as Bi/In/Ag oxides (EP 30 837) is also known. Finally, the principle is also applied to the dehydrogenation, dehydrocyclization and dehydroaromatization of paraffin hydrocarbons for gasoline refinement (U.S. Pat. No. 4,396,537 with Co/P oxide catalysts).

EP 397 637 and 403 462 disclose using the principle of the process for the oxidative dehydrogenation of paraffin hydrocarbons and alkylaromatics. According to these publications, reducible metal oxides selected from the group consisting of V, Cr, Mn, Fe, Co, Pb, Bi, Mo, U and Sn are applied to carriers comprising clays, zeolites and oxides of Ti, Zr, Zn, Th, Mg, Ca, Ba, Si and Al and used. V/MgO is particularly preferred.

Although a high yield can be obtained with these catalysts, very pronounced gasification (total combustion) occurs in the initial phase of the dehydrogenation when the hydrocarbon comes into contact with the freshly regenerated and therefore particularly active catalyst. Apart from the loss of raw materials, in addition the amount of oxygen consumed is considerably more than for the straightforward dehydrogenation, so that a large part of the oxygen carrier is prematurely exhausted and the cycle times unnecessarily become shorter.

SUMMARY OF THE INVENTION

It is an object of the present invention to provide an oxygen-carrying catalyst which permits higher conversions than the non-oxidative dehydrogenation and at the same time substantially avoids the disadvantageous behavior of the catalysts of the oxidative dehydrogenation in the initial phase, so that the selectivity is increased and additional process engineering steps, for example partial preliminary reduction of the oxygen carrier, can be dispensed with. It is a further object of the present invention to prepare a particularly hard catalyst which withstands the mechanical stress in industrial reactors without disintegrating.

We have found that these objects are achieved and that reducible metal oxides, such as oxides of Bi, V, Ce, Fe, In, Ag, Cu, Co, Mn, Pb, Sn, Mo, W, As and Sb, preferably Bi, Ce and V oxides, particularly preferably $Bi_2O_3$ or $CeO_2$, on a titanium dioxide carrier can be used as particularly advantageous oxygen-carrying catalysts for the oxidative dehydrogenation carried out in the absence of free oxidizing agent. We have also found that the addition of an alkali metal and/or alkaline earth metal, preferably Li, Na or Cs, in particular K, particularly effectively suppresses the initial gasification and permits large increases in the selectivity and in the yield of dehydrogenated product. The addition of alkaline earth metals and rare earth metals is also effective, lanthanum being particularly advantageous.

DETAILED DESCRIPTION OF THE PREFERRED EMBODIMENTS

A preferred catalyst contains 3–30, preferably 5–20, % by weight of $K_2O$, 5–50, preferably 10–30, % by weight of $Bi_2O_3$, and $TiO_2$ in the amount required to complete the balance.

Another preferred catalyst contains 3–30, preferably 5–20, % by weight of $Cs_2O$, 5–50, preferably 10–30, % by weight of $Bi_2O_3$, and $TiO_2$ in the amount required to complete the balance.

Another advantageous catalyst contains 3–40, preferably 5–30, % by weight of $La_2O_3$, 5–50, preferably 10–30, % by weight of $Bi_2O_3$, and $TiO_2$ in the amount required to complete the balance.

A further advantageous catalyst contains 0–30, preferably 5–20, % by weight of $Cs_2O$, 0–30, preferably 5–20, % by weight of $K_2O$, 0–40, preferably 5–30, % by weight of $La_2O_3$, 5–50, preferably 10–30, % by weight of $Bi_2O_3$, and $TiO_2$ in the amount required to complete the balance. An advantageous effect is also achieved by the joint use of, for example, Cs/La.

The above ratios are based on the prepared catalyst in the most stable or the stated oxidation state in each case. Hence, it is not intended to make any statement about the actual binding ratios and there is no intention of restricting the invention in this respect; for example, calcination may also result in the formation of phases which correspond to higher oxidation states of chromium, such as chromates or dichromates of potassium or of bismuth.

The catalyst can be prepared by conventional methods, such as dry blending, suspension, impregnation, precipitation, spray drying, etc. The ingredients may be used, for example, in the form of their oxides, hydroxides, carbonates, acetates, nitrates or generally water-soluble salts with organic or inorganic anions, which are converted into the corresponding oxides on heating (calcination). For example, transition metal complexes may also be used. The calcination is carried out at, typically, above 200° C. (up to 1000° C.), preferably from 200 to 800° C., in particular from 400 to 700° C.

The dehydrogenation reaction requires a temperature of from 200 to 800° C., preferably from 350 to 550° C., and atmospheric or slightly reduced or superatmospheric pressure, for example from 100 mbar to 10 bar, preferably from 500 mbar to 2 bar, at an LHSV of from 0.01 to 20 $h^{-1}$, preferably from 0.1 to 5 $h^{-1}$. In addition to the hydrocarbon to be hydrogenated, diluents, for example $CO_2$, $N_2$, noble gases or steam, may be present. The regeneration of the reduced catalyst requires temperatures of from 300 to 900° C., preferably from 400 to 800° C., the oxidizing agent used being, for example, $N_2O$ or an oxygen-containing gas. Here too, diluents may be present in the reactor feed. Suitable regenerating gases are, for example, air, air having a low oxygen content or $N_2O$ mixtures.

The regeneration can be operated at reduced, atmospheric or superatmospheric pressure. Pressures of from 500 mbar to 10 bar are preferred.

When lanthanum is used, $La_2O_3$ should not be used as a starting material. Instead, compounds containing organic radicals, preferably lanthanum acetate, should be used, calcination of said compounds leading to finely divided $La_2O_3$ having a large surface area.

EXAMPLE 1

60 g of $TiO_2$ are dry-blended with 33.22 g of basic bismuth carbonate $Bi_2CO_5$ (containing 81% by weight of Bi) and 14.67 g of $K_2CO_3$, and the procedure is continued as described below (Comparative Experiment 2). The catalyst contains 10% by weight of $K_2O$, 30% by weight of $Bi_2O_3$ and 60% by weight of $TiO_2$.

EXAMPLE 2

65 g of $TiO_2$ are dry-blended with 27.69 g of basic bismuth carbonate $Bi_2CO_5$ (containing 81% by weight of Bi) and 14.67 g of $K_2CO_3$, and the procedure is continued as described above. The catalyst contains 10% by weight of $K_2O$, 25% by weight of $Bi_2O_3$ and 65% by weight of $TiO_2$.

EXAMPLE 3

60 g of $TiO_2$ are dry-blended with 27.69 g of basic bismuth carbonate $Bi_2CO_5$ (containing 81% by weight of Bi) and 22.0 g of $K_2CO_3$, and the procedure is continued as described above. The catalyst contains 15% by weight of $K_2O$, 25% by weight of $Bi_2O_3$ and 60% by weight of $TiO_2$.

EXAMPLE 4

55 g of $TiO_2$ are dry-blended with 27.69 g of basic bismuth carbonate $Bi_2CO_5$ (containing 81% by weight of Bi) and 29.34 g of $K_2CO_3$, and the procedure is continued as described above. The catalyst contains 20% by weight of $K_2O$, 25% by weight of $Bi_2O_3$ and 55% by weight of $TiO_2$.

EXAMPLE 5

60 g of $TiO_2$ are dry-blended with 33.2 g of basic bismuth carbonate $Bi_2CO_5$ (containing 81% by weight of Bi) and 11.65 g of $Cs_2CO_3$, and the procedure is continued as described above. The catalyst contains 10% by weight of $Cs_2O$, 30% by weight of $Bi_2O_3$ and 60% by weight of $TiO_2$.

EXAMPLE 6

60 g of $TiO_2$ are dry-blended with 27.69 g of basic bismuth carbonate $Bi_2CO_5$ (containing 81% by weight of Bi) and 17.34 g of $Cs_2CO_3$, and the procedure is continued as described above. The catalyst contains 15% by weight of $Cs_2O$, 25% by weight of $Bi_2O_3$ and 60% by weight of $TiO_2$.

EXAMPLE 7

55 g of $TiO_2$ are dry-blended with 27.69 g of basic bismuth carbonate $Bi_2CO_5$ (containing 81% by weight of Bi) and 14.67 g of $K_2CO_3$ and 11.56 g of $Cs_2CO_3$, and the procedure is continued as described above. The catalyst contains 10% by weight of $Cs_2O$, 10% by weight of $K_2O$, 25% by weight of $Bi_2O_3$ and 55% by weight of $TiO_2$.

EXAMPLE 8

75 g of $TiO_2$ are dry-blended with 83.05 g of basic bismuth carbonate $Bi_2CO_5$ (containing 81% by weight of Bi), 36.68 g of $K_2CO_3$ and 161.53 g of lanthanum acetate $C_6H_9LaO_6$.aq (containing 39.56% by weight of La), and the procedure is continued as described above. The catalyst contains 10% by weight of $K_2O$, 30% by weight of $La_2O_3$, 30% by weight of $Bi_2O_3$ and 30% by weight of $TiO_2$.

COMPARATIVE EXPERIMENT 1 (according to EP 397637)

100 g of $SiO_2$ powder D11-10 from BASF are calcined at 500° C. for 3 hours. A solution of 102.5 g of $Fe(NO_3)_3.9H_2O$ in demineralized water is added to 85 g of the calcined $SiO_2$ until a final weight of 216 g is reached. The mixture is left to stand for 18 hours at room temperature, filtered and dried at 110° C. for 18 hours. Thereafter, it is heated at a rate of 30° C./h to 600° C. and calcined for 10 hours at 600° C. The catalyst is in powder form and contains 20% by weight of $Fe_2O_3$ and 80% by weight of $SiO_2$.

COMPARATIVE EXPERIMENT 2 (according to EP 397637)

336.3 g of ammonium metavanadate and 900 g of magnesium oxide are stirred into 8 l of water and then stirred vigorously for 1 hour. The mixture is then spray-dried. The spray-dried powder obtained is treated in a kneader for 2 hours, a little water and extrusion assistant being kneaded into the material. The kneaded material is then extruded to give 3 mm solid extrudates. The extrudates are dried for 16 hours at 120° C. and then calcined for 4 hours at 600° C. Uniformly yellow extrudates having low hardness are obtained. For the reactor experiments, a 0.05–0.1 mm chip fraction is separated off by sieving. The catalyst contains 22.5% by weight of $V_2O_5$ and 77.5% by weight of MgO.

COMPARATIVE EXPERIMENT 3

100 g of MgO powder and 58.1 g of $NH_4VO_3$ powder are dry-blended for 1 hour. The mixture is then kneaded in a kneader for 2.5 hours. Thereafter, the kneaded material is extruded to give 3 mm solid extrudates. The extrudates are dried for 2 hours at 120° C. and then calcined for 2 hours at 500° C. For the reactor experiments, a 0.05–0.1 mm chip fraction is separated off by sieving. XRD shows only the lines of $V_2O_5$ and MgO. The catalyst contains 31% by weight of $V_2O_5$ and 69% by weight of MgO.

COMPARATIVE EXPERIMENT 4

100 g of $TiO_2$ powder (DT-51 from BASF AG) are initially taken, and the procedure is continued according to Comparative Experiment 2. The catalyst consists of pure $TiO_2$.

COMPARATIVE EXPERIMENT 5

276.85 g of basic bismuth carbonate are initially taken and the procedure is continued according to the comparative experiment. The catalyst consists of pure $Bi_2O_3$.

COMPARATIVE EXPERIMENT 6

200 g of $TiO_2$ are dry-blended with 129.2 g of basic bismuth carbonate $Bi_2CO_5$ (containing 81% by weight of Bi), and the procedure is continued according to Comparative Experiment 2. The catalyst contains 63% by weight of $TiO_2$ and 37% by weight of $Bi_2O_3$.

COMPARATIVE EXPERIMENT 7

200 g of $TiO_2$ are dry-blended with 58.6 g of $NH_4VO_3$, and the procedure is continued according to Comparative Experiment 2. The catalyst contains 19% by weight of $V_2O_5$ and 81% by weight of $TiO_2$.

The hardness of the catalysts with respect to cutting is determined using a 3 mm solid extrudate, measuring the force in N required to cut through the extrudate with a sharp knife (blade width 0.6 mm).

The catalytic oxidative dehydrogenation of ethylbenzene to styrene is carried out in a pulsed reactor at 500° C. A pulsed stream of pure ethylbenzene is passed through a microfixed bed (catalyst weight: 0.3 g), and the resulting reaction products are determined quantitatively by gas chromatography for each pulse. Between two successive ethylbenzene pulses (about 1.5 minutes), helium flows through the reactor. An individual pulse contains 380 µg of ethylbenzene. The flow rate of the carrier gas is 21.5 ml/min. In this way, the behavior of the catalyst as a function of time can be monitored without dead times from the beginning with high time resolution.

At the beginning of the reaction, the catalyst is highly active, so that high, virtually quantitative conversions of ethylbenzene are observed. In the further course of the reaction, the selectivity with respect to styrene improves steadily until a final value is reached. However, with progressing duration of the experiment, the catalyst is increasingly deactivated at the rate at which its oxygen content is consumed, so that the conversion decreases. Regeneration is carried out after from 90 to 200 pulses, depending on the catalyst. The styrene yield as the product of selectivity and conversion generally passes through a gentle maximum. The yield listed in the table is based on this maximum value.

After the end of the dehydrogenation reaction, the feed is changed over to an air stream of 25 ml/min, and the catalyst is regenerated for about 1 hour at 500° C. This is followed by the next cycle. A plurality of cycles are investigated in each case.

The results of the examples/experiments are shown in the table below. The table contains a summary of the catalysts prepared, of the relative ratios of the components, of the hardness with respect to cutting and of the results of the tests (mean values from several experiments) for the dehydrogenation of ethylbenzene in a fixed-bed reactor.

The following conclusions may be drawn from the table:

The prior art systems are very active and permit a high maximum styrene yield. The decisive disadvantage is the pronounced initial gasification, which leads to enormous losses of ethylbenzene and depletes the oxygen reservoir of the catalyst. In particular, the initial ethylbenzene pulses are completely combusted (100% gasification to useless carbon dioxide), so that the theoretical initial selectivity with respect to styrene is zero for the initial pulses.

In contrast, the novel systems exhibit a substantially lower level of gasification while likewise having very high activity. Thus, the initial gasification (1st pulse) is only 30% by weight, compared with 100% by weight according to the prior art.

The styrene yield is substantially above that which can be obtained by means of nonoxidative dehydrogenation, this being the case at a lower reaction temperature.

As shown in Comparative Experiments 1 and 2, the preparation method is important in the case of the known catalysts. It is evident that the known spray-dried catalyst is substantially better than the dry-blended one.

However, the spray drying step in the catalyst preparation is a time-consuming and energy-intensive step which entails relatively high production costs. In the spray drying of MgO, the amount of water which must be added per gram of solid is higher than in the case of $TiO_2$, so that this process step takes place more rapidly with $TiO_2$ than with MgO.

The styrene selectivity of the novel catalyst at the maximum is comparable with the prior art, the catalyst preparation by dry-blending requiring substantially less time and substantially less expensive apparatus.

Although the novel catalyst produces slightly larger amounts of the biproducts benzene and toluene in the initial phase (instead of gas, as in the prior art), these amounts then rapidly decrease in the course of the reaction. The formation of benzene and toluene presents no problems compared with $CO_2$ formation, since toluene is a saleable product and benzene can be recycled to the ethylbenzene preparation and hence neither is lost. The novel catalyst is therefore also superior to the prior art in this respect, regardless of the fact that the average styrene yield or the total styrene yield is more advantageous than in the case of the known catalysts.

The decisive advantage of the novel system is the substantially reduced initial gasification, which permits enormous gains in the initial styrene selectivity compared with the prior art.

The novel catalyst is furthermore particularly abrasion-resistant. This has advantages for the mechanical handling of the catalysts (transport, installation in and removal from the reactor) and with regard to the mechanical load to which the catalysts are subjected in the fixed bed, and it must also be taken into account that the reoxidation results in the liberation of considerable quantities of heat which subject the catalyst to considerable mechanical stress. With the same preparation method, the novel catalyst (Examples 1 to 7) has substantially better mechanical strength compared with the Comparative Experiments 1 and 2.

alkenylaromatic, which process comprises: providing a redox catalyst, which serves as an oxygen carrier, the redox catalyst being prepared by admixing catalytic component bismuth oxide and a titanium oxide carrier in the presence of lanthanum and an additional catalytic component comprising a compound of a number of the group consisting of alkali metals and alkaline earth metals;

oxidatively dehydrogenating the alkylaromatic with the redox catalyst to produce a corresponding alkenylaromatic in a first reaction step, the redox catalyst being reduced in this step; and reoxidizing the reduced redox catalyst with an oxygen-containing gas in a second reaction step.

2. A process as claimed in claim 1, wherein the catalyst contains an inorganic binder.

3. A process as claimed in claim 1, wherein the first and the second reaction steps take place alternately in terms of time or at alternate places and the catalyst is contained in a fixed bed reactor.

4. A process as claimed in claim 3, wherein decoupling of the steps is effected by periodically switching the reactor inlet stream between starting material and oxidizing agent.

5. A process as claimed in claim 4, wherein the spatial decoupling of the steps is effected with the use of a circu-

TABLE

| Example | Catalyst | Amounts by weight [% by wt] | Cutting hardness N | Conversion [% by wt] | Selectivity [% by wt] | Yield [% by wt] |
|---|---|---|---|---|---|---|
| | | | | (at styrene maximum) | | |
| 1 | $Bi_2O_3/TiO_2$ | 37:63 | 34 | 42 | 81 | 34 |
| 2 | $V_2O_5/TiO_2$ | 19:81 | 15 | 43 | 95 | 40 |
| 3 | $K_2O/Bi_2O_3/TiO_2$ | 10:30:60 | 41 | 75 | 92 | 69 |
| | | | | 96 | 88 | 84 |
| 4 | $K_2O/Bi_2O_3/Ti_2$ | 10:25:65 | 33 | 94 | 90 | 84 |
| 5 | $K_2O/Bi_2O_3/TiO_2$ | 15:25:60 | 38 | 97 | 93 | 90 |
| 6 | $K_2O/Bi_2O_3/TiO_2$ | 20:25:55 | 22 | 96 | 92 | 89 |
| 7 | $Cs_2O/Bi_2O_3/TiO_2$ | 10:30:60 | 39 | 89 | 89 | 79 |
| | | | | 96 | 85 | 82 |
| 8 | $Cs_2O/Bi_2O_3/TiO_2$ | 15:25:60 | 34 | 94 | 89 | 84 |
| 9 | $K_2O/Cs_2O/Bi_2O_3/TiO_2$ | 10:10:25:55 | 30 | 98 | 92 | 89 |
| 10 | $K_2O/La_2O_3/Bi_2O_3/TiO_2$ | 10:30:30:30 | 8 | 95 | 91 | 86 |
| | | | | 99 | 93 | 92 |
| Comparison 1 | $V_2O_5/MgO$ | 22:78 | 0 | 99 | 94 | 93 |
| Comparison 2 | 2 $V_2O_5/MgO$ | 31:69 | 22 | 92 | 89 | 82 |
| Comparison 3 | $TiO_2$ DT-51 | 100 | 22 | 22 | 68 | 15 |
| Comparison 4 | $Bi_2O_3$ | 100 | 4 | B8 | | 6 |

| Example | Initial selectivity [% by weight] | Initial gasification [% by weight] 1st/10th/20th pulse | Residence time [sec] |
|---|---|---|---|
| 1 | 2/39/38 | 96/30/38 | 0.2 |
| 2 | 0/42/67 | 100/23/5 | 0.2 |
| 3 | 69/89/92 | 23/5/3 | 0.2 |
| | 51/84/88 | 31/7/6 | 0.4 |
| 4 | 49/82/86 | 35/10/7 | 0.4 |
| 5 | 53/87/93 | 31/4/3 | 0.4 |
| 6 | 53/90/92 | 32/3/2 | 0.4 |
| 7 | 71/89/90 | 23/7/5 | 0.2 |
| | 48/75/79 | 36/15/12 | 0.4 |
| 8 | 43/78/63 | 45/13/10 | 0.4 |
| 9 | 55/89/92 | 30/3/2 | 0.4 |
| 10 | 57/88/90 | 30/4/3 | 0.2 |
| | 51/82/85 | 31/5/4 | 0.4 |
| Comparison 1 | 0/52/76 | 100/30/15 | 0.2 |
| Comparison 2 | 0/39/61 | 100/45/22 | 0.2 |
| Comparison 3 | 3/68/75 | 96/4/3 | 0.4 |
| Comparison 4 | | 100/6/5 | 0.2 |

We claim:

1. A process for the catalytic oxidative dehydrogenation of an alkylaromatic to yield the corresponding lating fluidized bed, by circulating catalyst particles cyclically between a dehydrogenation reactor and a regeneration reactor.

6. A process as claimed in claim 3, wherein the catalyst is contained in a fixed bed reactor and a flushing phase, in which a flushing gas flows through the fixed bed reactor, is introduced between the steps.

7. A process as claimed in claim 6, wherein the flushing gas used is $CO_2$, $N_2$, $H_2O$ or a noble gas.

8. A process as claimed in claim 1, wherein ethylbenzene is dehydrogenated to styrene.

9. A process as claimed in claim 1, wherein the dehydrogenation is carried out at from 200 to 800° C. and at from 100 mbar to 10 bar at a liquid hourly space velocity (LHSV) of from 0.01 to 20 $h^{-1}$.

10. A process as defined in claim 1, wherein the redox catalyst comprises from 5 to 50% by weight of bismuth (3) oxide and from 3 to 30% by weight of $K_2O$ or $Cs_2O$, the remainder being titanium oxide and lanthanum, with the proviso that the sum of the percentages by weight is 100.

11. The process of claim 10, wherein the redox catalyst additionally comprises 5 to 30% by weight of lanthanum oxide, with the proviso that the sum of the percentages by weight is 100.

* * * * *

UNITED STATES PATENT AND TRADEMARK OFFICE
CERTIFICATE OF CORRECTION

PATENT NO.: 5,902,918

DATED: May 11, 1999

INVENTOR(S): HAGEMEYER et al.

It is certified that error appears in the above-identified patent and that said Letters Patent is hereby corrected as shown below:

Col. 8, claim 11, line 63, delete "additionally".

Signed and Sealed this

Seventh Day of September, 1999

Q. TODD DICKINSON

Attest:

Attesting Officer

Acting Commissioner of Patents and Trademarks